US011730863B2

(12) United States Patent
Ofek et al.

(10) Patent No.: US 11,730,863 B2
(45) Date of Patent: Aug. 22, 2023

(54) ANTIMICROBIAL CATHETER ASSEMBLIES AND METHODS THEREOF

(71) Applicant: C. R. Bard, Inc., Murray Hill, NJ (US)

(72) Inventors: Gidon Ofek, Honolulu, HI (US); Giridhar Thiagarajan, Salt Lake City, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 466 days.

(21) Appl. No.: 16/460,888

(22) Filed: Jul. 2, 2019

(65) Prior Publication Data
US 2020/0000972 A1    Jan. 2, 2020

Related U.S. Application Data

(60) Provisional application No. 62/693,327, filed on Jul. 2, 2018.

(51) Int. Cl.
*A61L 29/10*    (2006.01)
*A61L 29/14*    (2006.01)
*A61M 25/00*    (2006.01)

(52) U.S. Cl.
CPC ............. *A61L 29/106* (2013.01); *A61L 29/14* (2013.01); *A61M 25/0009* (2013.01);
(Continued)

(58) Field of Classification Search
CPC ........ A61L 29/08; A61L 29/106; A61L 29/14; A61L 2420/02; A61L 2300/404;
(Continued)

(56) References Cited

U.S. PATENT DOCUMENTS

| 4,603,152 A | * | 7/1986 | Laurin | ................... A61L 29/085 |
| | | | | 604/265 |
| 4,933,178 A | | 6/1990 | Capelli | |

(Continued)

FOREIGN PATENT DOCUMENTS

| WO | 95/18637 A1 | 7/1995 | | |
| WO | WO-9518637 A1 | * 7/1995 | ............. | A61L 27/54 |

(Continued)

OTHER PUBLICATIONS

PCT/US2019/040414 filed Jul. 2, 2019 International Search Report and Written Opinion dated Sep. 27, 2019.

*Primary Examiner* — Bhisma Mehta
*Assistant Examiner* — Robert F Allen
(74) *Attorney, Agent, or Firm* — Rutan & Tucker LLP

(57) ABSTRACT

An antimicrobial catheter assembly can include a hub, a catheter tube connected to the hub, at least one extension leg connected to the hub, and a non-eluting antimicrobial coating on an internal or external surface of the catheter assembly. The hub includes at least one hub lumen defining a corresponding hub portion of a fluid pathway through the catheter assembly. The catheter tube includes at least one catheter-tube lumen defining a corresponding catheter-tube portion of the fluid pathway through the catheter assembly. The extension leg can include an extension-leg lumen defining a corresponding extension-leg portion of the fluid pathway through the catheter assembly. The antimicrobial coating can include a copper-based layer between a corrosion-preventing layer and the internal or external surface of the catheter assembly, an adhesion-promoting layer between the copper-based layer and the internal or external surface of the catheter assembly, or a combination thereof.

20 Claims, 12 Drawing Sheets

(52) U.S. Cl.
CPC .... *A61M 25/0045* (2013.01); *A61M 25/0097* (2013.01); *A61L 2420/02* (2013.01); *A61M 2205/0205* (2013.01); *A61M 2205/0238* (2013.01)

(58) Field of Classification Search
CPC .......... A61L 2420/08; A61M 25/0045; A61M 25/0097; A61M 2205/0205; A61M 2205/0238
See application file for complete search history.

(56) References Cited

U.S. PATENT DOCUMENTS

| | | | |
|---|---|---|---|
| 5,516,480 A | 5/1996 | Krall et al. | |
| 5,520,664 A * | 5/1996 | Bricault, Jr. | A61F 2/30767 604/174 |
| 6,287,484 B1 | 9/2001 | Hausslein et al. | |
| 6,322,588 B1 | 11/2001 | Ogle et al. | |
| 6,333,093 B1 | 12/2001 | Burrell et al. | |
| 6,368,611 B1 | 4/2002 | Whitbourne et al. | |
| 6,436,422 B1 | 8/2002 | Trogolo et al. | |
| 6,585,767 B1 | 7/2003 | Holley et al. | |
| 6,620,460 B2 | 9/2003 | Oldiges et al. | |
| 6,949,598 B2 | 9/2005 | Terry | |
| 7,097,850 B2 | 8/2006 | Chappa et al. | |
| 7,147,625 B2 | 12/2006 | Sarangapani et al. | |
| 7,357,949 B2 | 4/2008 | Trogolo et al. | |
| 7,476,698 B2 | 1/2009 | Wagener et al. | |
| 7,645,824 B2 | 1/2010 | Hendriks et al. | |
| 7,736,730 B2 | 6/2010 | Jung et al. | |
| 7,829,029 B2 | 11/2010 | Zumeris et al. | |
| 7,906,132 B2 | 3/2011 | Ziegler et al. | |
| 7,951,853 B2 | 5/2011 | Ismail et al. | |
| 8,178,120 B2 | 5/2012 | Vandesteeg et al. | |
| 8,309,216 B2 | 11/2012 | Ohrlander et al. | |
| 8,361,553 B2 | 1/2013 | Karandikar et al. | |
| 8,394,448 B2 | 3/2013 | Lachner | |
| 8,394,494 B2 | 3/2013 | Ohrlander et al. | |
| 8,454,984 B2 | 6/2013 | Krongauz et al. | |
| 8,470,453 B2 | 6/2013 | Ohrlander et al. | |
| 8,497,017 B2 | 7/2013 | Ohrlander et al. | |
| 8,563,020 B2 | 10/2013 | Uhlmann et al. | |
| 8,579,990 B2 | 11/2013 | Priewe | |
| 8,753,561 B2 | 6/2014 | Lee et al. | |
| 8,764,960 B2 | 7/2014 | Chung et al. | |
| 8,765,256 B2 | 7/2014 | Ohrlander et al. | |
| 8,834,686 B2 | 9/2014 | McClure et al. | |
| 8,841,000 B2 | 9/2014 | Gong et al. | |
| 9,016,221 B2 | 4/2015 | Brennan et al. | |
| 9,017,797 B2 | 4/2015 | Goelling | |
| 9,289,378 B2 | 3/2016 | Karandikar et al. | |
| 9,339,588 B2 | 5/2016 | Ohrlander et al. | |
| 9,393,350 B2 | 7/2016 | McGrath et al. | |
| 9,402,933 B2 | 8/2016 | Heidenau et al. | |
| 9,522,507 B2 | 12/2016 | Ganey et al. | |
| 9,603,964 B2 | 3/2017 | Dubey et al. | |
| 9,629,946 B2 | 4/2017 | Johansson et al. | |
| 2004/0039437 A1 | 2/2004 | Sparer et al. | |
| 2004/0220534 A1 | 11/2004 | Martens et al. | |
| 2005/0058835 A1 | 3/2005 | Howdle et al. | |
| 2005/0234516 A1 | 10/2005 | Gueret | |
| 2006/0083710 A1 | 4/2006 | Joerger et al. | |
| 2006/0134313 A1 | 6/2006 | Guggenbichler et al. | |
| 2006/0182954 A1 | 8/2006 | Bowman et al. | |
| 2007/0259427 A1 | 11/2007 | Storey et al. | |
| 2008/0020210 A1 | 1/2008 | Griffin et al. | |
| 2009/0035342 A1 | 2/2009 | Karandikar et al. | |
| 2009/0324738 A1 | 12/2009 | Krongauz | |
| 2010/0074932 A1 | 3/2010 | Talsma | |
| 2010/0113871 A1 | 5/2010 | Dias et al. | |
| 2010/0190004 A1 | 7/2010 | Gibbins et al. | |
| 2010/0215643 A1 | 8/2010 | Clevenger et al. | |
| 2010/0227052 A1 | 9/2010 | Carter et al. | |
| 2011/0152843 A1 | 6/2011 | Wedlin et al. | |
| 2012/0070685 A1 | 3/2012 | Kloss et al. | |
| 2012/0083750 A1 | 4/2012 | Sansoucy | |
| 2012/0294919 A1 | 11/2012 | Jaynes et al. | |
| 2014/0154297 A1 | 6/2014 | Krongauz et al. | |
| 2014/0276493 A1 | 9/2014 | Leung et al. | |
| 2015/0196685 A1 | 7/2015 | Schwartz et al. | |
| 2015/0258248 A1 | 9/2015 | Baek | |
| 2015/0290357 A1 | 10/2015 | Chu | |
| 2015/0351851 A1 | 12/2015 | Deselle et al. | |
| 2015/0352320 A1 * | 12/2015 | Eddy | A61M 25/00 604/29 |
| 2016/0121077 A1 * | 5/2016 | Ingalls | B23P 15/00 604/527 |
| 2016/0144602 A1 | 5/2016 | Levasseur et al. | |
| 2016/0250390 A1 | 9/2016 | Ohrlander et al. | |
| 2016/0287758 A1 * | 10/2016 | Thiagarajan | A61M 25/0045 |
| 2017/0086746 A1 * | 3/2017 | Ofek | A61B 5/042 |

FOREIGN PATENT DOCUMENTS

| | | |
|---|---|---|
| WO | 2014138885 A1 | 9/2014 |
| WO | 2014204407 A1 | 12/2014 |
| WO | 2016040529 A1 | 3/2016 |
| WO | 2016132288 A1 | 8/2016 |

* cited by examiner

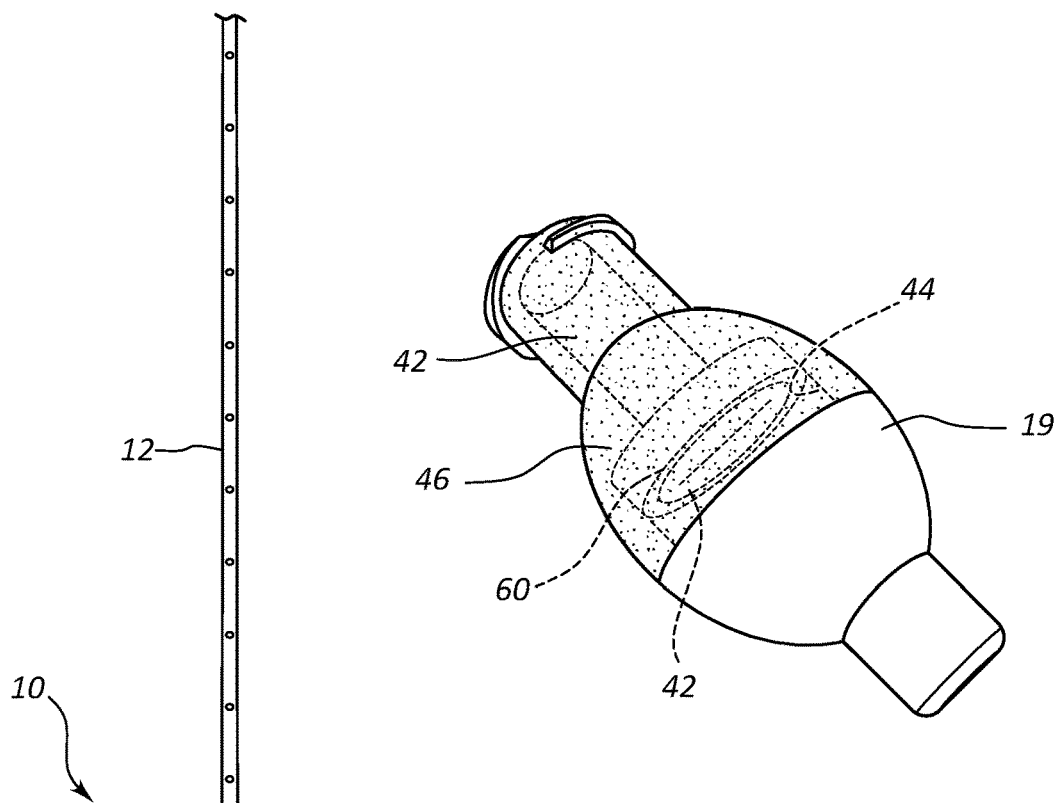
FIG. 10
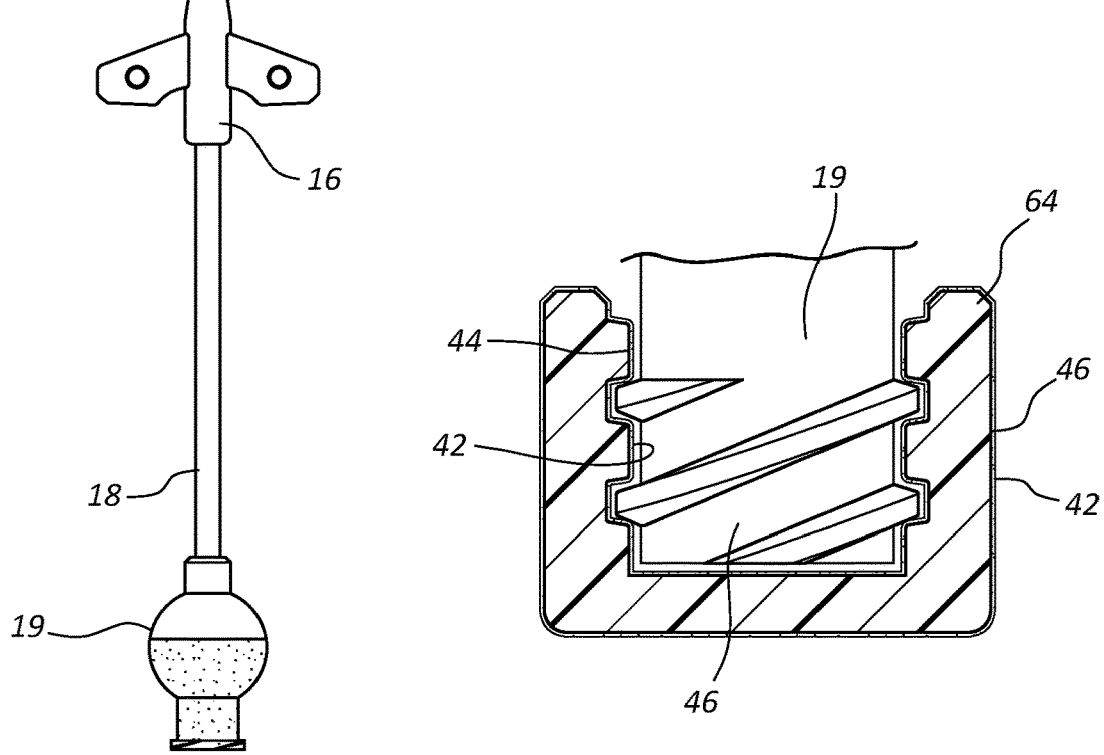
FIG. 9
FIG. 11

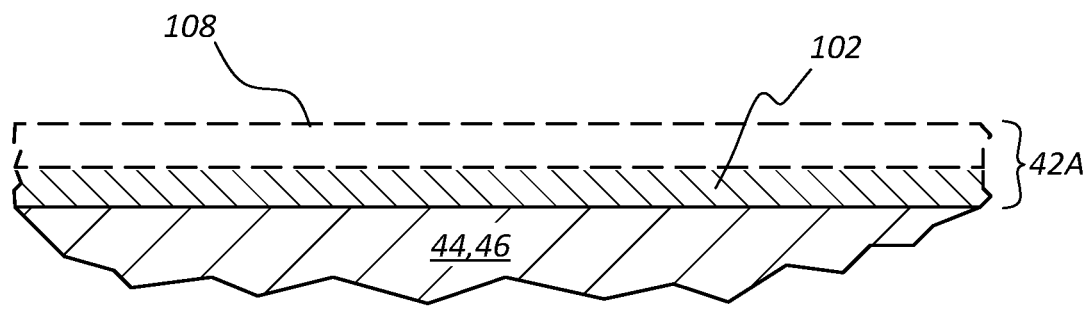
FIG. 14A
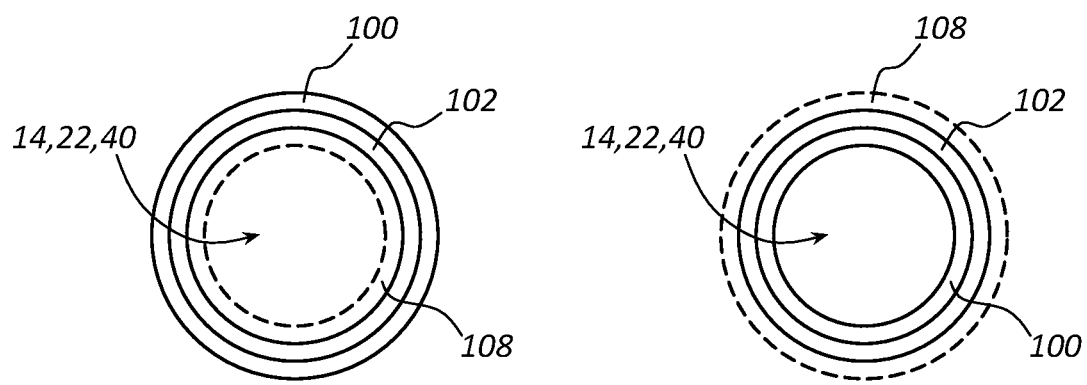
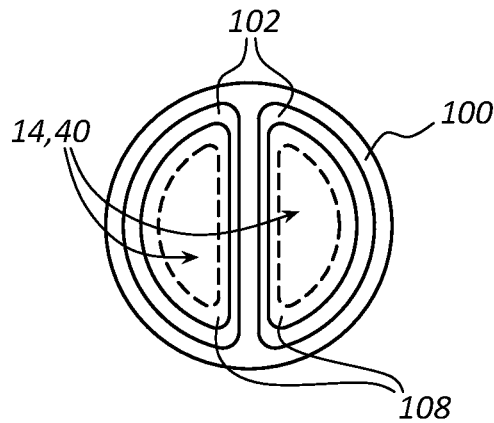
FIG. 14B
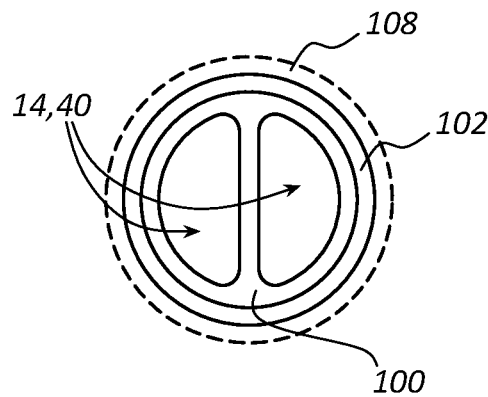
FIG. 14C
FIG. 14D
FIG. 14E

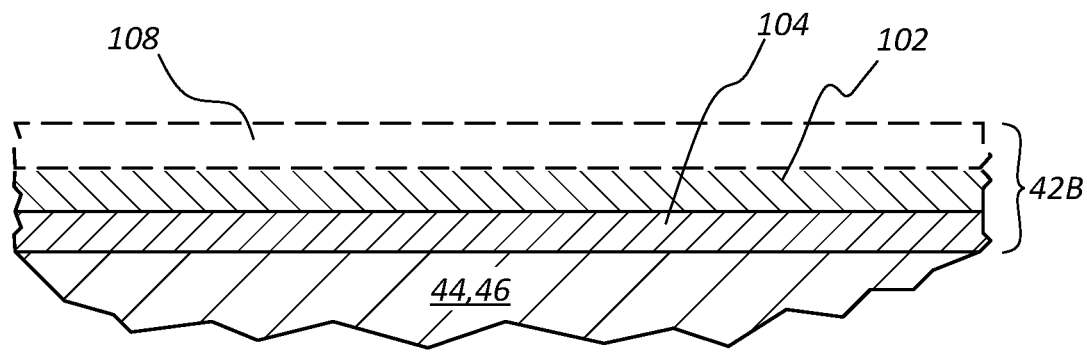
FIG. 15A
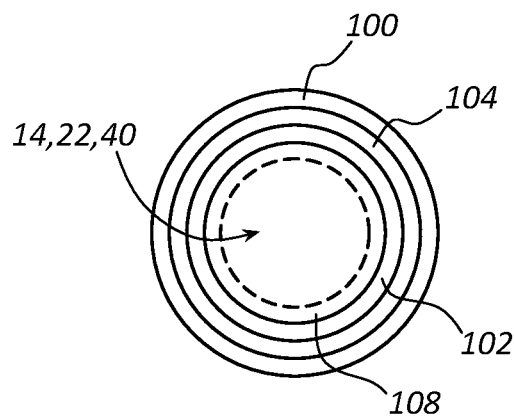 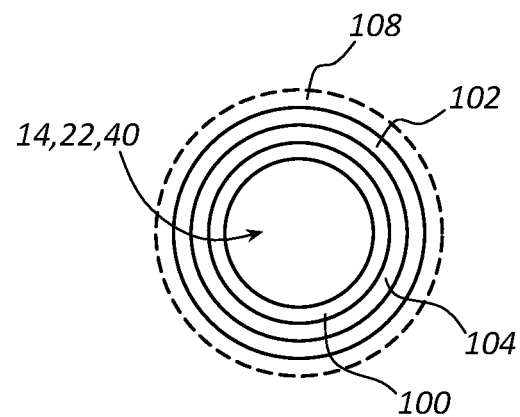
FIG. 15B FIG. 15C

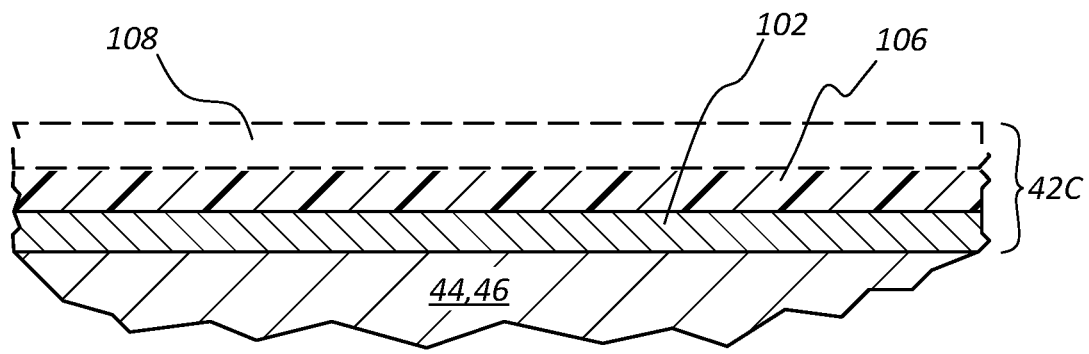
FIG. 16A
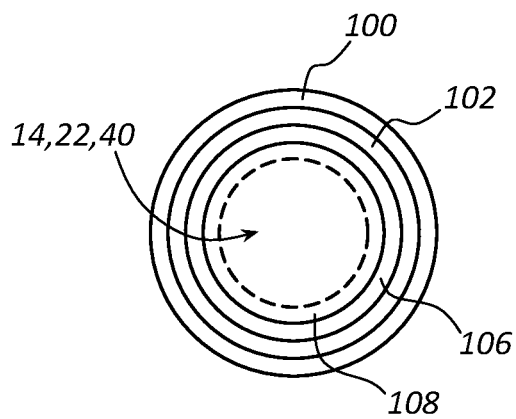 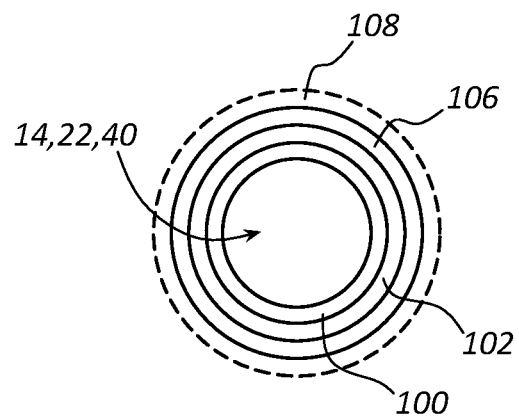
FIG. 16B  FIG. 16C

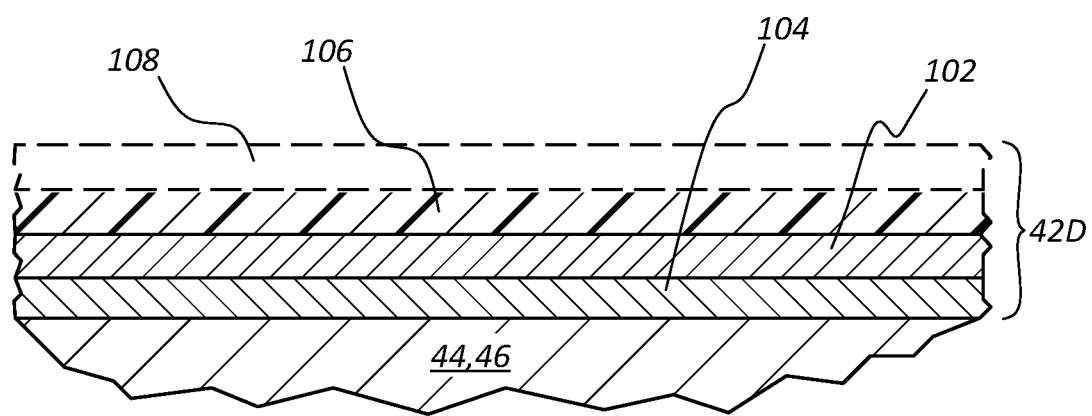
FIG. 17A
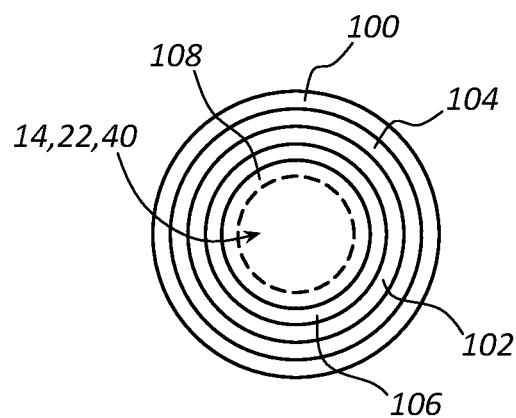      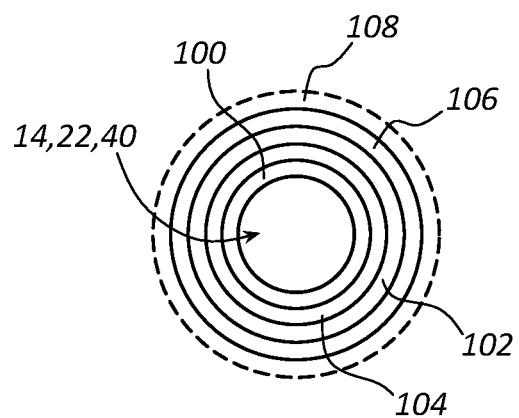
FIG. 17B                FIG. 17C

ANTIMICROBIAL CATHETER ASSEMBLIES AND METHODS THEREOF

PRIORITY

This application claims the benefit of priority to U.S. Provisional Application No. 62/693,327, filed Jul. 2, 2018, which is incorporated by reference in its entirety into this application.

BACKGROUND

Catheters are among the most commonly used medical devices. For example, central venous catheters ("CVCs") are routinely placed within a patient's vascular system for quickly delivering fluids including nutrients or drugs (e.g., chemotherapeutic agents) or accurately measuring central venous pressure. Often, CVCs are left in place for extended periods of time. However, complications can occur when CVCs are left in place such as catheter-related sepsis ("CRS"), which results when bacteria colonized on such catheters migrate into the blood and cause the inflammatory immune response characteristic of CRS. Replacing such catheters at frequent intervals is one potential solution to CRS, but frequently replacing the catheters often results in replacing sterile catheters that need not to be replaced—and additional catheterization carries with it its own risks. In view of the foregoing, antimicrobial catheters are needed to prevent bacteria colonies that can migrate into the blood. Disclosed herein are antimicrobial catheter assemblies and methods thereof that address the foregoing.

SUMMARY

Disclosed herein is an antimicrobial catheter assembly including, in some embodiments, a hub, a catheter tube connected to the hub, at least one extension leg connected to the hub, and a non-eluting antimicrobial coating on an internal surface of the catheter assembly, an external surface of the catheter assembly, or both the internal and external surfaces of the catheter assembly. The hub includes at least one hub lumen defining a corresponding hub portion of a fluid pathway through the catheter assembly. The catheter tube includes at least one catheter-tube lumen defining a corresponding catheter-tube portion of the fluid pathway through the catheter assembly. The extension leg includes an extension-leg lumen defining a corresponding extension-leg portion of the fluid pathway through the catheter assembly. The antimicrobial coating is a composite of two or more layers. The antimicrobial coating includes a copper-based layer between a corrosion-preventing layer and the internal or external surface of the catheter assembly, an adhesion-promoting layer between the copper-based layer and the internal or external surface of the catheter assembly, or a combination thereof.

In some embodiments, the adhesion-promoting layer includes an adhesion-promoting metal.

In some embodiments, the adhesion-promoting metal promotes adhesion of the copper-based layer to a polymer selected from polyurethane, polycarbonate, polyethylene, polypropylene, polyvinyl chloride, and silicone.

In some embodiments, the adhesion-promoting metal is selected from gold, palladium, and titanium.

In some embodiments, the copper-based layer is substantially pure copper, a copper alloy of copper and gold, palladium, zinc, or tin, or a copper matrix composite of copper and tungsten.

In some embodiments, the corrosion-preventing layer includes a corrosion-resistant metal selected from gold, palladium, and titanium.

In some embodiments, the antimicrobial coating includes two layers, the two layers being the adhesion-promoting layer and the copper-based layer.

In some embodiments, the antimicrobial coating includes two layers, the two layers being the copper-based layer and the corrosion-preventing layer.

In some embodiments, the antimicrobial coating includes three layers, the three layers being the adhesion-promoting layer, the copper-based layer, and the corrosion-preventing layer.

In some embodiments, the antimicrobial coating is on the internal surface of the catheter assembly including the hub lumen defining the corresponding hub portion of the fluid pathway through the catheter assembly.

In some embodiments, the antimicrobial coating is on the internal surface of the catheter assembly including the extension-leg lumen defining the corresponding extension-leg portion of the fluid pathway through the catheter assembly.

In some embodiments, the antimicrobial coating is on the external surface of the catheter assembly including an abluminal surface of the extension leg between at least proximal and distal end portions of the extension leg.

In some embodiments, the antimicrobial coating is on the external surface of the catheter assembly including an abluminal surface of a transcutaneous region of the catheter tube.

In some embodiments, the antimicrobial catheter assembly further includes at least one Luer connector connected to the extension leg. The antimicrobial coating is on the internal surface of the catheter assembly including an internal surface of the Luer connector in fluid communication with the fluid pathway, an external surface of the catheter assembly including an external surface of the Luer connector, or a combination thereof.

Also disclosed herein is an antimicrobial catheter assembly including, in some embodiments, a bifurcated hub, a catheter tube connected to the hub, a pair of extension legs connected to the hub, a pair of Luer connectors connected to the extension legs, and a non-eluting antimicrobial coating on an internal surface of the catheter assembly, an external surface of the catheter assembly, or both the internal and external surfaces of the catheter assembly. The hub includes a pair of hub lumens defining corresponding hub portions of a pair of fluid pathways through the catheter assembly. The catheter tube includes a pair of catheter-tube lumens defining corresponding catheter-tube portions of the pair of fluid pathways through the catheter assembly. Each extension leg of the pair of extension legs includes an extension-leg lumen defining a corresponding extension-leg portion of the pair of fluid pathways through the catheter assembly. The antimicrobial coating is a composite of two or more layers. The antimicrobial coating includes a copper-based layer between a corrosion-preventing layer and the internal or external surface of the catheter assembly, an adhesion-promoting layer between the copper-based layer and the internal or external surface of the catheter assembly, or a combination thereof.

In some embodiments, the adhesion-promoting layer promotes adhesion of the copper-based layer to a polymer selected from polyurethane, polycarbonate, polyethylene, polypropylene, polyvinyl chloride, and silicone. The adhesion-promoting layer includes a metal selected from gold, palladium, and titanium.

In some embodiments, the copper-based layer is substantially pure copper, a copper alloy of copper and gold, palladium, zinc, or tin, or a copper matrix composite of copper and tungsten.

In some embodiments, the corrosion-preventing layer includes a corrosion-resistant metal selected from gold, palladium, and titanium.

In some embodiments, the antimicrobial coating includes two layers. The two layers are either the adhesion-promoting layer and the copper-based layer or the copper-based layer and the corrosion-preventing layer.

In some embodiments, the antimicrobial coating includes three layers. The three layers are the adhesion-promoting layer, the copper-based layer, and the corrosion-preventing layer.

In some embodiments, the antimicrobial coating is on the internal surface of the catheter assembly including the hub lumen defining the corresponding hub portions of the pair of fluid pathways through the catheter assembly.

In some embodiments, the antimicrobial coating is on the internal surface of the catheter assembly including the extension-leg lumens defining the corresponding extension-leg portions of the pair of fluid pathways through the catheter assembly.

In some embodiments, the antimicrobial coating is on the internal surface of the catheter assembly including an internal surface of each Luer connector, which internal surface defines a corresponding Luer-connector portion of the pair of fluid pathways through the catheter assembly. Alternatively or additionally, the antimicrobial coating is on the external surface of the catheter assembly including an external surface of each Luer connector.

In some embodiments, the antimicrobial coating is on the external surface of the catheter assembly including abluminal surfaces of the pair of extension legs between at least proximal and distal end portions of each extension leg.

In some embodiments, the antimicrobial coating is on the external surface of the catheter assembly including an abluminal surface of a transcutaneous region of the catheter tube.

Also disclosed herein is a method of manufacturing an antimicrobial catheter assembly including, in some embodiments, applying a non-eluting antimicrobial coating to an internal surface, an external surface, or both the internal and external surfaces of one or more components of the catheter assembly; and connecting the components of the catheter assembly to form the catheter assembly. The antimicrobial coating is a composite of two or more layers including a copper-based layer between a corrosion-preventing layer and the internal or external surface to which the antimicrobial coating is applied, an adhesion-promoting layer between the copper-based layer and the internal or external surface to which the antimicrobial coating is applied, or a combination thereof.

In some embodiments, applying the antimicrobial coating includes applying the adhesion-promoting layer to the internal or external surface of any component of the one or more components of the catheter assembly. The adhesion-promoting layer is applied to the foregoing internal or external surface by physical vapor deposition, chemical vapor deposition, electrodeposition, or electroless deposition of a metal selected from gold, palladium, and titanium. The internal or external surface to which the adhesion-promoting layer is applied includes a polymer selected from polyurethane, polycarbonate, polyethylene, polypropylene, polyvinyl chloride, and silicone.

In some embodiments, applying the antimicrobial coating includes applying the copper-based layer to the internal or external surface of any component of the one or more components of the catheter assembly. The copper-based layer is applied to the foregoing internal or external surface by physical vapor deposition, chemical vapor deposition, electrodeposition, or electroless deposition of copper, a copper alloy, or a copper matrix composite. The internal or external surface to which the copper-based layer is applied includes a polymer selected from polyurethane, polycarbonate, polyethylene, polypropylene, polyvinyl chloride, and silicone or the adhesion-promoting layer.

In some embodiments, applying the antimicrobial coating includes applying the corrosion-preventing layer to the internal or external surface of any component of the one or more components of the catheter assembly. The corrosion-preventing layer is applied to the foregoing internal or external surface by physical vapor deposition, chemical vapor deposition, electrodeposition, or electroless deposition of gold, palladium, or titanium. The internal or external surface to which the corrosion-preventing layer is applied includes the copper-based layer.

In some embodiments, connecting the components of the catheter assembly includes inserting a catheter tube into a hub, inserting at least one extension leg into the hub, and inserting the extension leg into at least one Luer connector to form the catheter assembly. The catheter assembly has a fluid pathway defined by internal surfaces of a catheter-tube lumen, a hub lumen, and an extension-leg lumen.

These and other features of the concepts provided herein will become more apparent to those of skill in the art in view of the accompanying drawings and following description, which describe particular embodiments of such concepts in greater detail.

DRAWINGS

FIG. 1 provides an illustration of a catheter assembly in accordance with some embodiments.

FIG. 2 provides an illustration of a bifurcated hub of the catheter assembly of FIG. 1.

FIG. 3 provides an illustration of a transcutaneous region of a catheter tube of the catheter assembly of FIG. 1.

FIG. 4 provides an illustration of a Luer connector of the catheter assembly of FIG. 1.

FIG. 9 provides an illustration of a catheter assembly in accordance with some embodiments.

FIG. 10 provides an illustration of a valved Luer connector of the catheter assembly of FIG. 9.

FIG. 11 illustrates a cross-section of a cap over an end portion of the Luer connector of FIG. 10.

Figure 12:
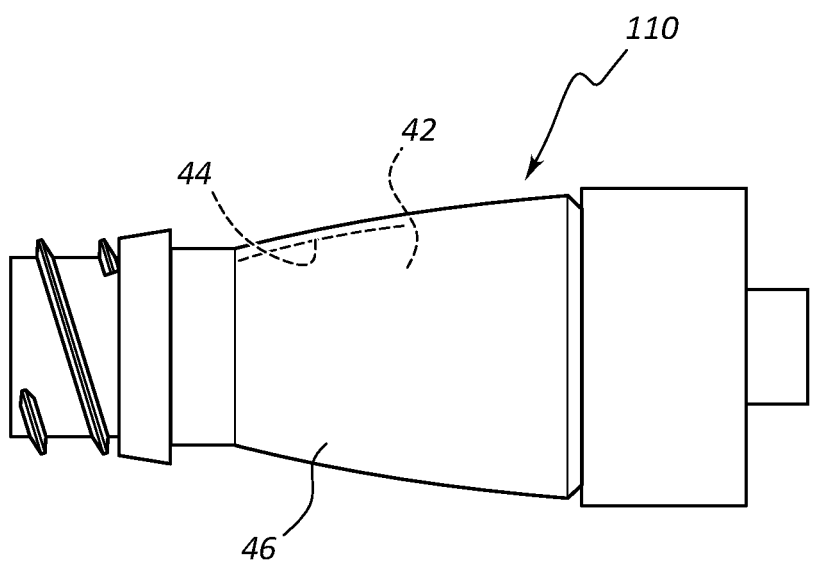

FIG. 12 provides an illustration of a needleless connector in accordance with some embodiments.

Figure 13:
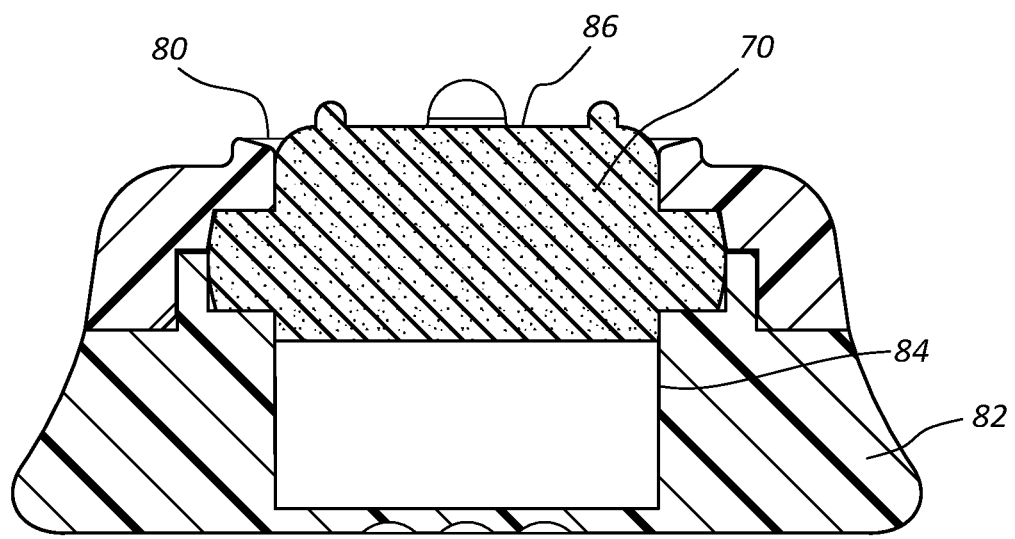

FIG. 13 provides an illustration of an implantable access port in accordance with some embodiments.

FIG. 14A illustrates a longitudinal cross-section of a portion of a medical device including an antimicrobial coating on a surface thereof in accordance with some embodiments.

FIG. 14B illustrates a transverse cross-section of a tubular portion of a medical device including an antimicrobial coating on a luminal surface thereof in accordance with some embodiments.

FIG. 14C illustrates a transverse cross-section of a tubular portion of a medical device including an antimicrobial coating on an abluminal surface thereof in accordance with some embodiments.

FIG. 14D illustrates a transverse cross-section of a dual-lumen catheter tube of a catheter assembly including an antimicrobial coating on a luminal surface thereof in accordance with some embodiments.

FIG. 14E illustrates a transverse cross-section of a dual-lumen catheter tube of a catheter assembly including an antimicrobial coating on an abluminal surface thereof in accordance with some embodiments.

FIG. 15A illustrates a longitudinal cross-section of a portion of a medical device including an antimicrobial coating on a surface thereof in accordance with some embodiments.

FIG. 15B illustrates a transverse cross-section of a tubular portion of a medical device including an antimicrobial coating on a luminal surface thereof in accordance with some embodiments.

FIG. 15C illustrates a transverse cross-section of a tubular portion of a medical device including an antimicrobial coating on an abluminal surface thereof in accordance with some embodiments.

FIG. 16A illustrates a longitudinal cross-section of a portion of a medical device including an antimicrobial coating on a surface thereof in accordance with some embodiments.

FIG. 16B illustrates a transverse cross-section of a tubular portion of a medical device including an antimicrobial coating on a luminal surface thereof in accordance with some embodiments.

FIG. 16C illustrates a transverse cross-section of a tubular portion of a medical device including an antimicrobial coating on an abluminal surface thereof in accordance with some embodiments.

FIG. 17A illustrates a longitudinal cross-section of a portion of a medical device including an antimicrobial coating on a surface thereof in accordance with some embodiments.

FIG. 17B illustrates a transverse cross-section of a tubular portion of a medical device including an antimicrobial coating on a luminal surface thereof in accordance with some embodiments.

FIG. 17C illustrates a transverse cross-section of a tubular portion of a medical device including an antimicrobial coating on an abluminal surface thereof in accordance with some embodiments.

Figure 18:
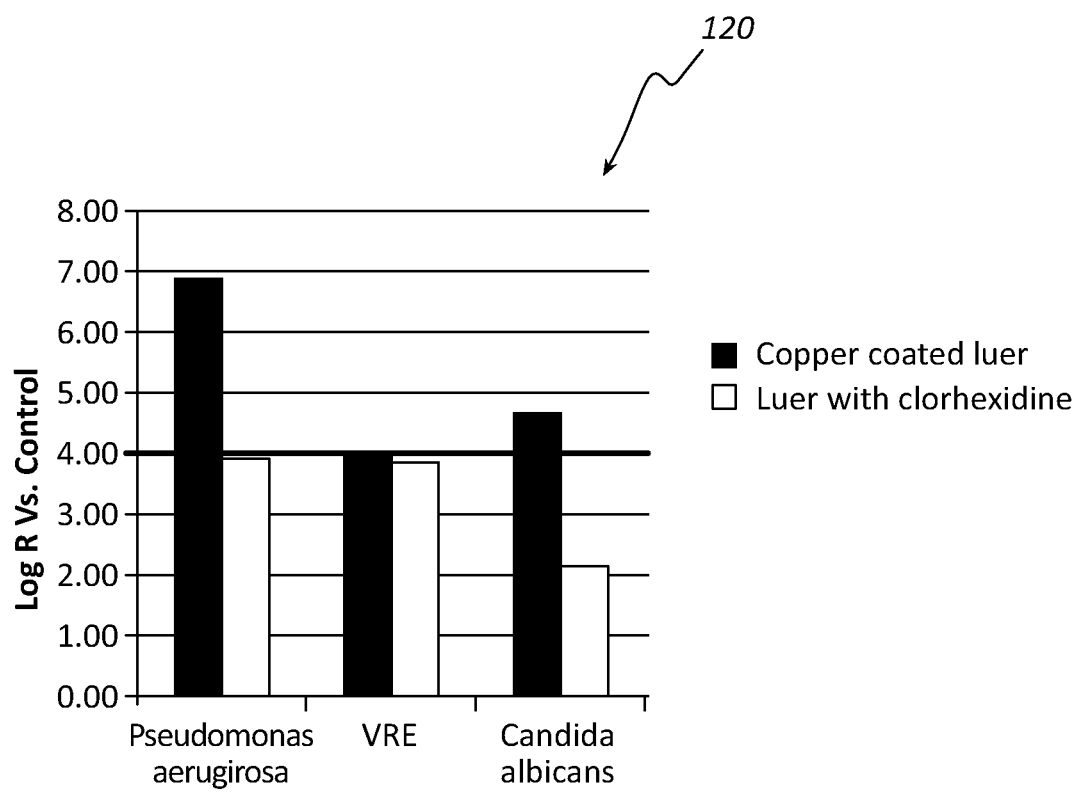

FIG. 18 is a chart comparing a copper-coated Luer connector to a chlorhexidine-coated Luer connector for a set of microbes.

Figure 19:
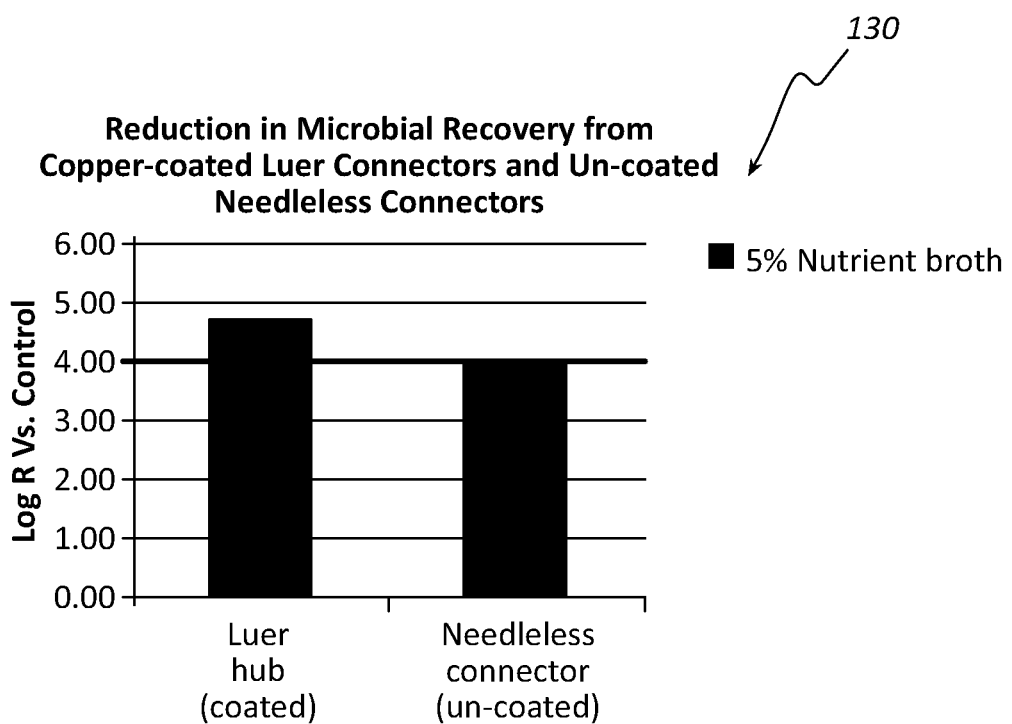

FIG. 19 is a chart comparing a copper-coated Luer connector to an uncoated needleless connector with respect to microbial recovery therefrom.

Figure 20:
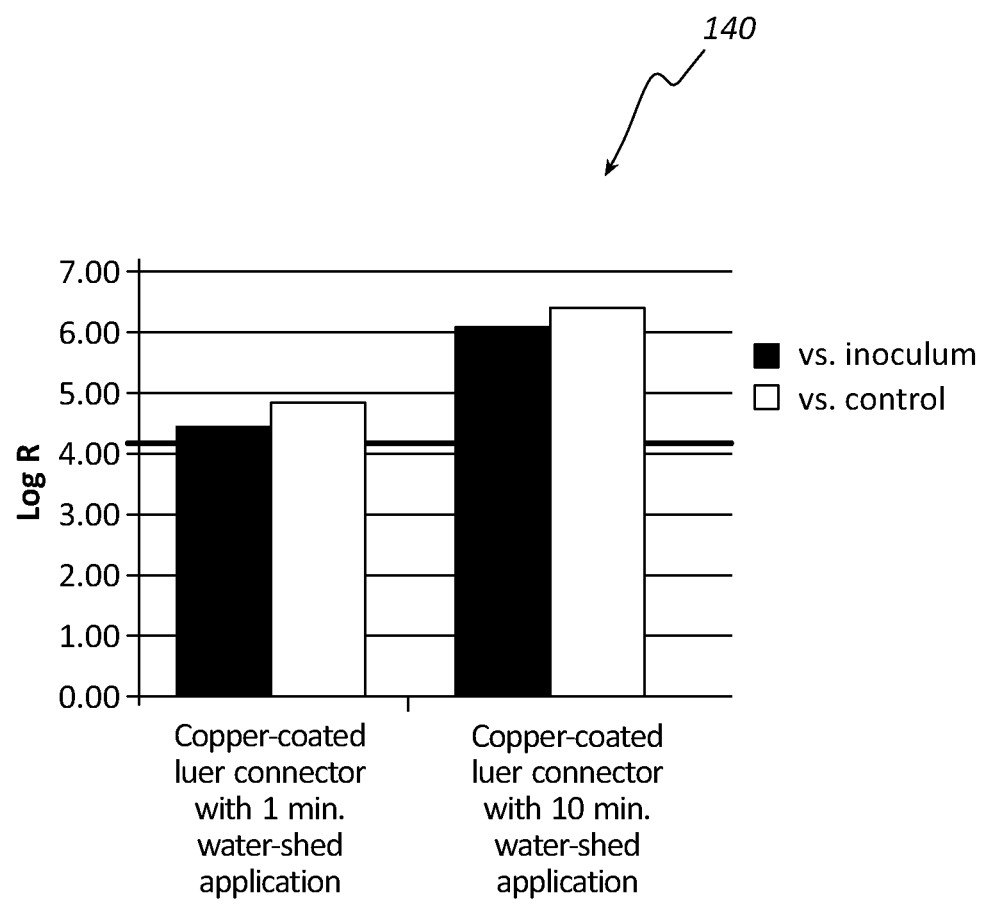

FIG. 20 is a chart comparing different applications of a water-shed layer to copper-coated Luer connectors.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

As set forth above, antimicrobial catheters are needed to prevent bacteria colonies that can migrate into the blood. Disclosed herein are antimicrobial catheter assemblies and methods thereof that address the foregoing.

For example, an antimicrobial catheter assembly is disclosed including, in some embodiments, a hub, a catheter tube connected to the hub, at least one extension leg connected to the hub, and a non-eluting antimicrobial coating on an internal surface of the catheter assembly, an external surface of the catheter assembly, or both the internal and external surfaces of the catheter assembly. The hub includes at least one hub lumen defining a corresponding hub portion of a fluid pathway through the catheter assembly. The catheter tube includes at least one catheter-tube lumen defining a corresponding catheter-tube portion of the fluid pathway through the catheter assembly. The extension leg includes an extension-leg lumen defining a corresponding extension-leg portion of the fluid pathway through the catheter assembly. The antimicrobial coating is a composite of two or more layers. The antimicrobial coating includes a copper-based layer between a corrosion-preventing layer and the internal or external surface of the catheter assembly, an adhesion-promoting layer between the copper-based layer and the internal or external surface of the catheter assembly, or a combination thereof.

These and other features will become more apparent to those of skill in the art in view of the accompanying drawings and the following description, which describe such embodiments in greater detail.

Antimicrobial Catheter Assemblies

Figure 1:
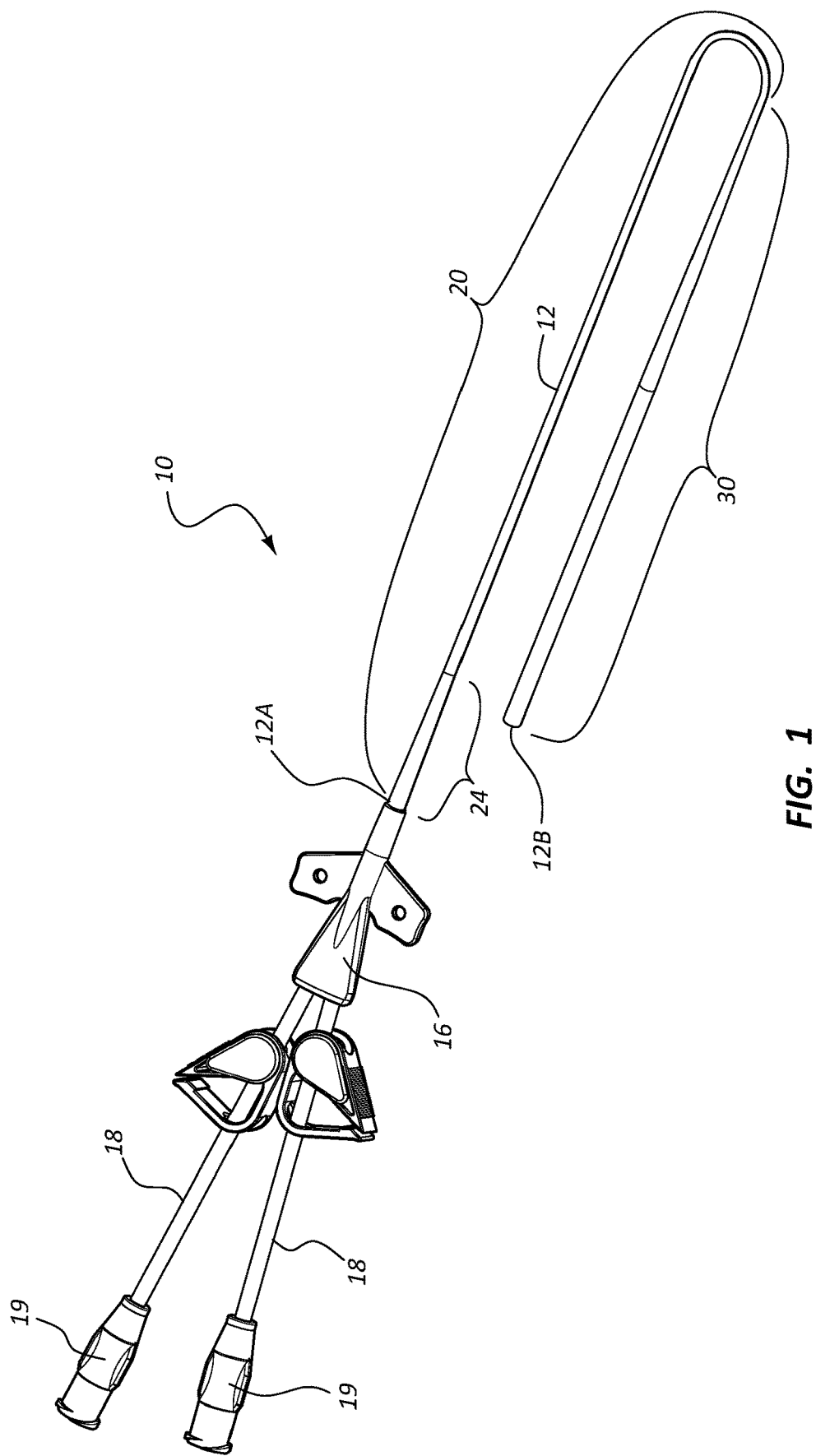

Reference is first made to FIGS. 1 and 9, each of which depict a catheter assembly ("catheter") 10 in accordance with some embodiments. As shown, the catheter 10 includes an elongate catheter tube 12 that extends between proximal and distal ends 12A, 12B. The catheter tube 12 includes a proximal portion 20 extending distally from the proximal end 12A and a distal portion 30 extending distally from a distal end of the proximal portion to the distal end 12B of the catheter tube 12. The catheter tube 12 of the catheter 10 shown in FIG. 1 defines two catheter-tube lumens 14 or a pair of catheter-tube lumens 14 configured for the passage of fluids therein, whereas the catheter tube 12 of the catheter 10 shown in FIG. 9 defines one catheter-tube lumen 14 or a single catheter-tube lumen 14 configured for the passage of fluids therein. Each catheter-tube lumen 14 of the foregoing catheter-tube lumens 14 is designated as catheter-tube lumen 14 in FIG. 5, which depicts a longitudinal cross-section of a catheter tube such as the catheter tube 12 of the catheter 10 in either FIG. 1 or FIG. 9. Each catheter-tube lumen 14 of the pair of catheter-tube lumens 14 is designated as catheter-tube lumen 14 in FIGS. 14D and 14E, which depict a transverse cross-section of a tubular portion of a two-lumen medical device such as the catheter tube 12 of the catheter 10 of FIG. 1. More than two catheter-tube lumens 14 such as three catheter-tube lumens are possible in other types of catheters.

Figure 3:
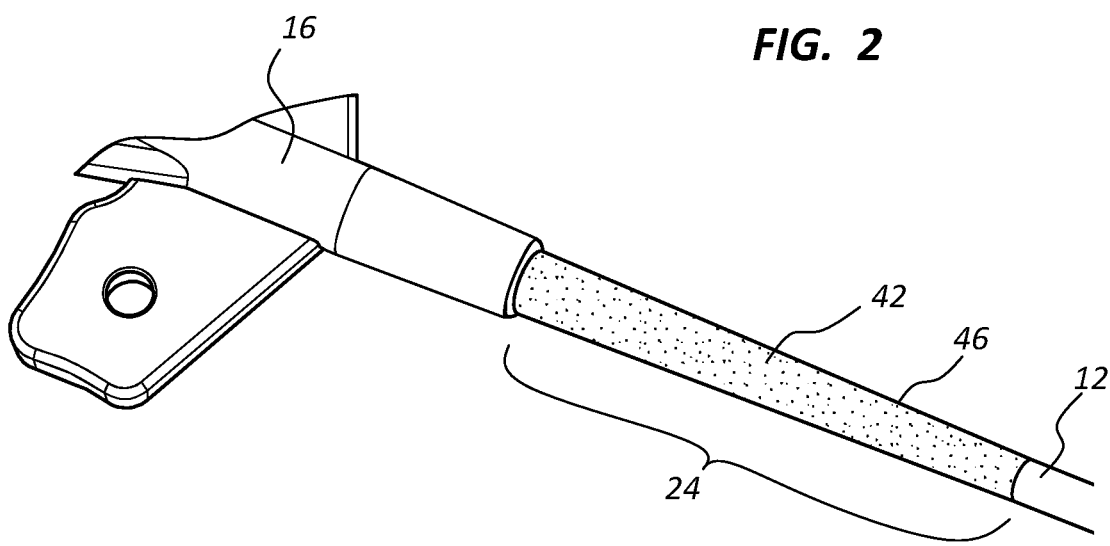
Figure 4:
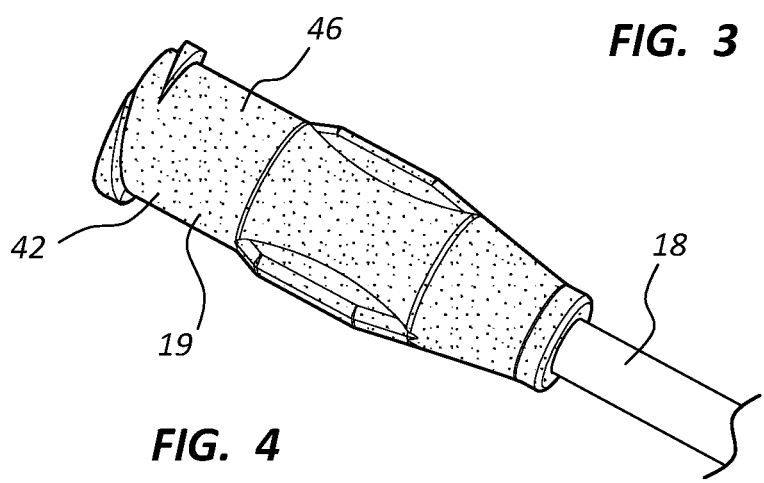

As shown in FIG. 3, the catheter tube 12 includes a tapered region 24 of the proximal portion 20 extending distally from the hub 16. The tapered region 24 of the catheter tube 12 is the portion of the catheter tube 12 that typically passes through the patient's skin at the insertion site before entering a vein or other vessel of the patient.

A hub 16 is operably connected to both the proximal end 12A of the catheter tube 12 and a number of extension legs 18, each of which is designated as extension leg 18 in FIGS. 1 and 9. The hub 16 provides a number of hub lumens 40 through the hub 16 equal to the number of catheter-tube lumens 14 through the catheter tube 12 and the number of extension legs 18 connected to the hub 16 of the catheter 10. The hub 16 of the catheter 10 shown in FIG. 1 is a bifurcated hub in that it defines two hub lumens 40 or a pair of hub lumens 40 configured for the passage of fluids therein, whereas the hub 16 of the catheter 10 shown in FIG. 9 defines one hub lumen 40 or a single hub lumen 40 configured for the passage of fluids therein. Each hub lumen 40 of the pair of hub lumens 40 is designated as hub lumen 40 in FIG. 2, which depicts the bifurcated hub 16 of the catheter 10 in FIG. 1, or FIG. 14D, which depicts a transverse cross-section of a tubular distal-end portion of the bifurcated hub 16 of the catheter 10 of FIG. 1. More than two hub lumens 40 such as three hub lumens 40 are possible in other types of catheters. Each extension leg 18 defines an extension-leg lumen 22 and includes a Luer connector 19 (or another suitable connector) connected to a proximal end thereof to enable a syringe or other device to operably connect with the catheter 10.

In light of the above, it is appreciated that various components of the catheter 10 define one or more fluid pathways through which fluid can travel through the catheter 10 to infuse fluids including nutrients or drugs into the vein, aspirate blood or other fluids from the vein, or both by way of the catheter 10. The fluid pathway of the catheter 10 is defined by the one or more extension-leg lumens 22, the one or more hub lumens 40 of the hub 16, and the one or more catheter-tube lumens 14 of the catheter tube 12. It is appreciated that additional or other components can contribute to defining a fluid pathway of a catheter in other embodiments, and that other invasive medical devices can include other types of fluid pathways.

Figure 2:
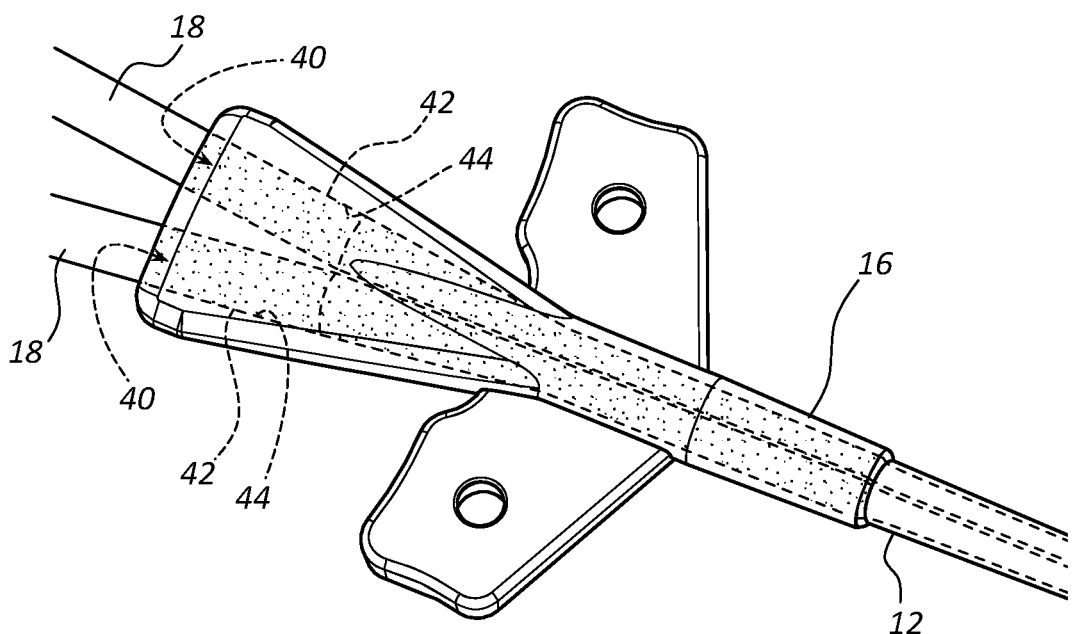

FIG. 2 depicts further details regarding the bifurcated hub 16 of the catheter 10 of FIG. 1. As shown, the bifurcated hub 16 defines the pair of hub lumens 40 thereof, which provide fluid communication between the pair of catheter-tube lumens 14 of the catheter tube 12 and the corresponding extension-leg lumens 22 of the pair of extension legs 18. Likewise, the hub 16 of the catheter 10 of FIG. 9 defines the single hub lumen 40 thereof, which provides fluid communication between the single catheter-tube lumen 14 of the catheter tube 12 and the corresponding extension-leg lumen 22 of the single extension leg 18. Together, the one or more hub lumens 40, the one or more catheter-tube lumens 14, and the one or more extension-leg lumens 22 define a substantial portion of the fluid pathway through the catheter 10.

Whether the hub 16 is that of the catheter 10 of FIG. 1 or FIG. 9, the hub 16 can be formed of a plastic such as a thermoset or a thermoplastic, a silicone, one or more metals, one or more ceramics, or glass. A plastic from which the hub 16 can be formed includes polyurethane, polycarbonate, polyvinyl chloride ("PVC"), polyethylene, or polypropylene. For example, ISOPLAST® available from the Lubrizol Corporation, Wickliffe, Ohio, is a thermoplastic polyurethane from which the hub 16 can be formed.

In accordance with some embodiments, one or more fluid pathways through the catheter 10 include a substantially non-eluting antimicrobial coating 42 on an internal surface 44 (e.g., a luminal surface) thereof or one or more portions of the internal surface 44 such as the internal surface 44 of the hub lumen 40, the catheter-tube lumen 14, the extension-leg lumen 22, or a combination thereof. Any hub lumen 40 of the hub 16 is typically difficult for traditional antimicrobial treatments to reach. As such, inclusion of the antimicrobial coating 42 on at least a portion of the internal surface 44 of one or more lumens 40 of the hub 16 improves the ability of the catheter 10 to resist microbial colonization. Alternatively or additionally to the foregoing, the antimicrobial coating 42 is on an external surface 46 (e.g., an abluminal surface) of the catheter 10 or one or more portions of the external surface 46 such as the external surface 46 of the hub 16, the catheter tube 12, the extension leg 18, or a combination thereof. The antimicrobial coating 42 is a composite including at least a copper-based layer configured to provide an antimicrobial effect for inhibiting the establishment or survival of microbes on a coated surface such as the internal surface 44 of the one or more fluid pathways of the catheter 10 or the external surface 46 of one or more components of the catheter 10. As such, any of a variety of surfaces of a medical device such as the catheter 10 of FIG. 1 or FIG. 9 can be coated with the antimicrobial coating 42, the variety of surfaces being either a part of or independent of the foregoing internal and external surfaces 44, 46 of the catheter 10.

"Substantially non-eluting" means that only a relatively small amount of a metal such as copper is released from the antimicrobial coating 42 into fluids surrounding the antimicrobial coating 42. In some embodiments, for example, the antimicrobial coating 42 releases copper particles resulting in a copper concentration of no more than about 1.5 ppm in a fluid such as a bodily fluid in contact with the antimicrobial coating 42. This release can vary according to various factors including surface composition of the medical device, the type of fluid the antimicrobial coating 42 is exposed to, thickness of one or more layers of the antimicrobial coating 42, the presence of an overcoat in the antimicrobial coating 42, etc.

FIGS. 14A, 15A, 16A, and 17A each illustrate a longitudinal cross-section of a portion of a medical device such as the catheter 10 including the antimicrobial coating 42 on a surface thereof in accordance with some embodiments. The portion of the medical device can be the catheter tube 12, the hub 16, or the one or more extension legs 18 of the catheter 10, and the surface can be the internal surface 44, the external surface 46, or both the internal and external surfaces 44, 46. FIGS. 14B-14E, 15B, 15C, 16B, 16C, 17B, and 17C illustrate transverse cross-sections of a tubular portion of a medical device such as the catheter 10 including the antimicrobial coating 42 in accordance with some embodiments. FIGS. 14B, 14D, 15B, 16B, and 17B illustrate the antimicrobial coating 42 on the internal or luminal surface 44 of the tubular portion of the medical device shown, whereas FIGS. 14C, 14E, 15C, 16C, and 17C illustrate the antimicrobial coating 42 on the external or abluminal surface 46 of the tubular portion of the medical device shown.

Again, the antimicrobial coating 42 is a composite of two or more layers. At a minimum, the antimicrobial coating 42 includes a copper-based layer 102. Optionally, the antimicrobial coating 42 includes an overcoat 108, wherein the copper-based layer 102 is between the surface of the medical device and the overcoat 108, thereby forming the antimicrobial coating 42A shown in FIG. 14A. FIG. 14B illustrates the antimicrobial coating 42A on the internal or luminal surface 44 of a tubular portion of a single-lumen medical device 100 such as the luminal surface 44 of the catheter tube 12, the distal end portion of the hub 16, or the extension leg 18 of the catheter 10 of FIG. 9, while FIG. 14C illustrates the antimicrobial coating 42A on the external or abluminal surface 46 of the foregoing tubular portions of the catheter 10. FIG. 14D illustrates the antimicrobial coating 42A on the internal or luminal surfaces 44 of a tubular portion of a dual-lumen medical device 100 such as the luminal surfaces 44 of the catheter tube 12 or the distal end portion of the hub 16 of the catheter 10 of FIG. 1, while FIG. 14E illustrates the antimicrobial coating 42A on the external or abluminal surfaces 46 of the foregoing tubular portions of the catheter 10. While not shown, the antimicrobial coating 42A can be on both the internal and external surfaces 44, 46 of the foregoing tubular portions the catheter 10.

The copper-based layer 102 is substantially pure copper, a copper alloy, or copper matrix composite. The copper alloy includes copper and gold (e.g., rose gold), palladium, zinc (e.g., brass), or tin (e.g., bronze). The copper matrix composite includes a copper matrix and tungsten dispersed in the copper matrix.

The overcoat 108 is configured to prevent tarnishing of the antimicrobial coating 42 by oxidation. The overcoat 108 includes Tarniban® manufactured by Technic, Inc., Providence, R.I.

In addition to the copper-based layer 102 of the antimicrobial coating 42, the antimicrobial coating 42 can include an adhesion-promoting layer 104, wherein the adhesion-promoting layer 104 is between the internal or external surface of the medical device and the copper-based layer 102, thereby forming the antimicrobial coating 42B shown in FIG. 15A. Optionally, the antimicrobial coating 42B includes the overcoat 108 such that the copper-based layer 102 is between the adhesion-promoting layer 104 and the overcoat 108. FIG. 15B illustrates the antimicrobial coating 42B on the internal or luminal surface 44 of a tubular portion of a single-lumen medical device 100 such as the luminal surface 44 of the catheter tube 12, the distal end portion of the hub 16, or the extension leg 18 of the catheter 10 of FIG. 9, while FIG. 15C illustrates the antimicrobial coating 42B on the external or abluminal surface 46 of the foregoing tubular portions of the catheter 10. The antimicrobial coating 42B is not shown on either the internal surfaces 44 or the external surface 46 of a tubular portion of a dual-lumen medical device 100 such as the catheter 10 of FIG. 1, but it should be understood the antimicrobial coating 42B can be applied to the internal surfaces 44 or the external surface 46 of such medical devices resulting in dual-lumen medical devices having transverse cross-sections analogous to those of FIGS. 14D and 14E with the antimicrobial coating 42B. While not shown, the antimicrobial coating 42B can be on both the internal and external surfaces 44, 46 of the foregoing tubular portions the catheter 10.

The adhesion-promoting layer 104 promotes adhesion of the copper-based layer 102 to the internal surface 44 or the external surface 46 of the medical device, which surface can be a polymer selected from polyurethane, polycarbonate, polyethylene, polypropylene, polyvinyl chloride, and silicone. The adhesion-promoting layer 104 includes an adhesion-promoting metal including a noble metal (e.g., gold, palladium, silver, iridium, or platinum), a metal having a relatively high resistance to corrosion (e.g., titanium), or an alloy of one of the foregoing metals.

In addition to the copper-based layer 102 of the antimicrobial coating 42, the antimicrobial coating 42 can include a corrosion-preventing layer 106, wherein the copper-based layer 102 is between the corrosion-preventing layer 106 and the internal or external surface of the medical device, thereby forming the antimicrobial coating 42C shown in FIG. 16A. Optionally, the antimicrobial coating 42C includes the overcoat 108 such that the corrosion-preventing layer 106 is between the copper-based layer 102 and the overcoat 108. FIG. 16B illustrates the antimicrobial coating 42C on the internal or luminal surface 44 of a tubular portion of a single-lumen medical device 100 such as the luminal surface 44 of the catheter tube 12, the distal end portion of the hub 16, or the extension leg 18 of the catheter 10 of FIG. 9, while FIG. 16C illustrates the antimicrobial coating 42C on the external or abluminal surface 46 of the foregoing tubular portions of the catheter 10. The antimicrobial coating 42C is not shown on either the internal surfaces 44 or the external surface 46 of a tubular portion of a dual-lumen medical device 100 such as the catheter 10 of FIG. 1, but it should be understood the antimicrobial coating 42C can be applied to the internal surfaces 44 or the external surface 46 of such medical devices resulting in dual-lumen medical devices having transverse cross-sections analogous to those of FIGS. 14D and 14E with the antimicrobial coating 42C. While not shown, the antimicrobial coating 42C can be on both the internal and external surfaces 44, 46 of the foregoing tubular portions the catheter 10.

The corrosion-preventing layer 106 prevents corrosion of the copper-based layer 102. The corrosion-preventing layer 106 includes a corrosion-resistant metal including a noble metal (e.g., gold, palladium), a metal having a relatively high resistance to corrosion (e.g., titanium), or an alloy of one of the foregoing metals. As set forth above, the copper-based layer 102 can include a copper alloy of copper and gold or palladium. Being as gold and palladium are noble metals, such a copper-based layer 102 is configured to have at least some resistance to corrosion. Therefore, the antimicrobial layer 42 need not have the corrosion-preventing layer 106 when the copper-based layer is a copper alloy of copper and gold or palladium.

The antimicrobial coating 42 can include both the adhesion-promoting layer 104 and the corrosion-preventing layer 106, wherein the copper-based layer 102 is between the adhesion-promoting layer 104 and the corrosion-preventing layer 106, and wherein the adhesion-promoting layer 104 is between the copper-based layer 102 and the internal or external surface of the medical device, thereby forming the antimicrobial coating 42D shown in FIG. 17A. Optionally, the antimicrobial coating 42D includes the overcoat 108 such that the corrosion-preventing layer 106 is between the copper-based layer 102 and the overcoat 108. FIG. 17B illustrates the antimicrobial coating 42D on the internal or luminal surface 44 of a tubular portion of a single-lumen medical device 100 such as the luminal surface 44 of the catheter tube 12, the distal end portion of the hub 16, or the extension leg 18 of the catheter 10 of FIG. 9, while FIG. 17C illustrates the antimicrobial coating 42D on the external or abluminal surface 46 of the foregoing tubular portions of the catheter 10. The antimicrobial coating 42D is not shown on either the internal surfaces 44 or the external surface 46 of a tubular portion of a dual-lumen medical device 100 such as the catheter 10 of FIG. 1, but it should be understood the antimicrobial coating 42D can be applied to the internal surfaces 44 or the external surface 46 of such medical devices resulting in dual-lumen medical devices having transverse cross-sections analogous to those of FIGS. 14D and 14E with the antimicrobial coating 42D. While not shown, the antimicrobial coating 42D can be on both the internal and external surfaces 44, 46 of the foregoing tubular portions the catheter 10.

The antimicrobial coating 42 is configured to not substantially elute metals such as copper into a fluid carried by a medical device such as the catheter 10 or a bodily fluid exposed to the medical device. Indeed, elution of copper from a substantially copper copper-based layer 102 of the antimicrobial coating 42 on an internal, fluid-carrying surface of the Luer connector 19 amounted to about 0.210 µg when the antimicrobial coating 42 was exposed to a solution of 0.9% saline and 0.157 µg ethanol for a period of about 24 hours. The amount of copper eluted from the Luer connector 19 represented approximately 0.009% of the total copper content of the antimicrobial coating 42 on the Luer connector, thus evidencing substantial non-elution.

Each layer of the antimicrobial coating 42 including the adhesion-promoting layer 104, the copper-based layer 102, or the corrosion-preventing layer 106 is applied to an internal or external surface of a medical device by physical vapor deposition, chemical vapor deposition, electrodeposition, or electroless deposition of a metal to produce a substantially uniform, relatively thin layer of the antimicrobial coating 42. Each layer of the antimicrobial coating 42 is sufficiently thin such that flaking or rubbing off a layer of the antimicrobial coating 42 does not occur under normal usage of the medical device including the antimicrobial coating 42. Each layer of the antimicrobial coating 42 can have a thickness less than about 1.0 µm, including a thickness less than about 0.8 µm, such as a thickness less than about 0.6 µm, for example, a thickness less than about 0.5 µm, which provides a thickness for the antimicrobial coating 42 ranging from about 2.0 µm for a two-layered antimicrobial coating 42 to about 3.0 µm for a three-layered antimicrobial coating 42. That said, each layer of the antimicrobial coating 42 is not limited to less than about 1.0 µm, and the antimicrobial coating 42 is not limited to a thickness less than about 2.0 µm to about 3.0 µm. Indeed, the thickness of the antimicrobial coating 42 can vary in accordance with a number of factors including the desired effective life of the antimicrobial coating 42, the desired level of antimicrobial efficacy for the antimicrobial coating 42, indwelling time for the medical device, size limitations of one or more fluid pathways to prevent occlusions in the one or more fluid pathways, or the like.

Other application techniques can be employed to deposit one or more layers of the antimicrobial coating 42 on an internal or external surface of a medical device including electroplating, ion beam deposition, or sputtering. Different surfaces upon which the antimicrobial coating 42 is applied benefit from certain application techniques. For example, metallic surfaces and plastic surfaces including conducting polymers benefit from electroplating the copper-based layer 102 thereon. Ceramic surfaces or the like benefit from spray coating the copper-based layer 102 thereon.

When the overcoat 108 of the antimicrobial coating 42 is present, the overcoat 108 is applied by immersing a component of a medical device including one or more other layers of the antimicrobial coating 42 in a solution containing butoxyethanol and butoxyethoxy ethanol for a predetermined time.

While the antimicrobial coating 42 is configured to maintain internal or external surfaces of a medical surface substantially free of microbes through contact killing of such microbes, other antimicrobial measures can be employed in conjunction with the antimicrobial coating 42. For example, the internal surfaces 44 of the hub lumens 40 of the bifurcated hub 16 can include the antimicrobial coating 42, while at least the internal surface 44 of the catheter-tube lumen 14 of the catheter tube 12 includes a different antimicrobial coating such as that provided by an antimicrobial solution. As such, the antimicrobial coating 42 can cooperate with other antimicrobial measures in same or different medical-device locations to provide antimicrobial protection.

As set forth above, the antimicrobial coating 42 is employed in a variety of medical-device locations including the internal or external surfaces of medical devices such as the catheter 10 of FIG. 1 or FIG. 9. FIGS. 2-8 and 10-13 give further detail in various non-limiting examples of such the medical-device locations the antimicrobial coating 42 can be employed.

As set forth above, FIG. 2 depicts the bifurcated hub 16 of the catheter 10 of FIG. 1, which bifurcated hub provides the pair of hub lumens 40 thereof for fluid communication between the pair of catheter-tube lumens 14 of the catheter tube 12 and the corresponding extension-leg lumens 22 of the pair of extension legs 18. Likewise, the hub 16 of the catheter 10 of FIG. 9 provides the single hub lumen 40 thereof for fluid communication between the single catheter-tube lumen 14 of the catheter tube 12 and the corresponding extension-leg lumen 22 of the single extension leg 18. The pair of hub lumens 40 or the single hub lumen 40 can include the antimicrobial coating 42 on the internal or luminal surface 44 thereof.

In FIG. 3, the external or abluminal surface 46 of the tapered portion 24 of the catheter tube 12 adjacent the bifurcated hub 16 can include the antimicrobial coating 42 thereon. The tapered portion 24 is also referred to as the "transcutaneous region" as this portion of the catheter tube 12 extends through a patient's skin and into the patient's vein or other vessel at the insertion site. The antimicrobial coating 42 of the external surface of the tapered region 24 is useful to prevent microbial migration from the skin at the insertion site to a remainder of the catheter tube 12 in the patient's vein or other vessel. It is appreciated that one or more internal surfaces 44 of the tapered portion 24 (e.g., luminal surfaces) can also include the antimicrobial coating 42—as well as other internal or external surfaces of the catheter tube 12.

FIGS. 4, 6, 7 and 8 show that the Luer connector 19 can include the antimicrobial coating 42 on the internal surface 44 in fluid communication with a remainder of the fluid pathway of the catheter 10, the external surface 46, or both the internal surface 44 and the external surface 46 of the Luer connector 19. Application of the antimicrobial coating 42 to the connector 19 helps prevent the formation and proliferation of microbes on the internal or external surfaces of the Luer connector including the antimicrobial coating 42. Connectors such as the Luer connector 19 can be especially susceptible to microbial contamination due to relatively extensive physical contact by clinicians or other users of the catheter 10. As such, the antimicrobial coating 42 can be especially suitable on the Luer connector 19 or other portions of medical devices that experience relatively extensive physical contact during a procedure.

Figure 8:
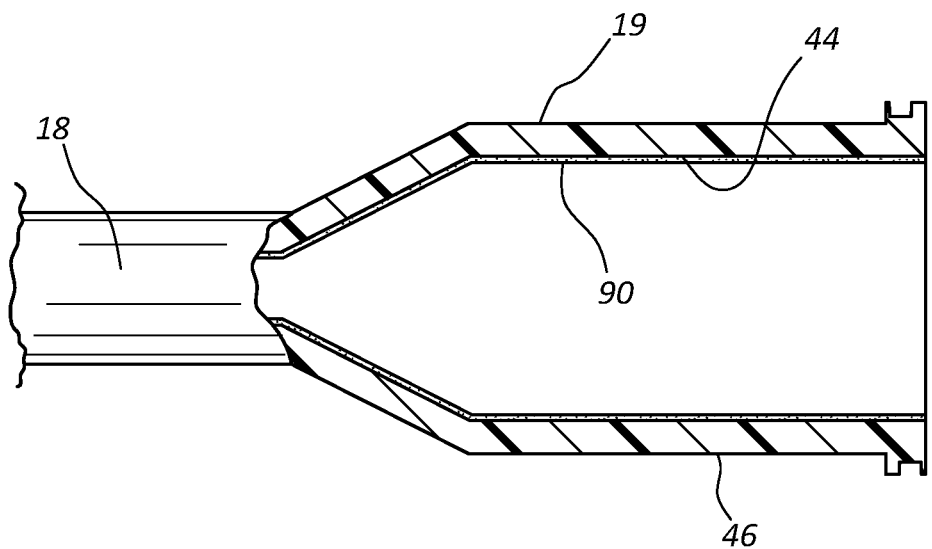
FIG. 8 illustrates a cross-section of a Luer connector of a catheter assembly in accordance with some embodiments.

As an alternative to the copper-based layer 102 of the antimicrobial layer 42, FIG. 8 shows the Luer connector 19 with a copper-containing insert 90 for the internal surface 44. The copper-containing insert 90 along with one or more additional layers of the antimicrobial layer 42 set forth above provides the substantially non-eluting antimicrobial coating 42 configured to provide a contact-killing antimicrobial effect, thereby protecting against the formation or proliferation of microbes therein. A variety of medical devices or components thereof can use such copper-containing inserts in one or more locations thereof to provide the copper-based layer 102 of the antimicrobial layer 42. The copper-containing insert 90 can be introduced to a medical or a component thereof (e.g., the Luer connector 19) by insert molding with the copper-containing insert 90. Such copper-containing insert can also be included in extruded components as well such the pair of extension legs 18 or the catheter tube 12 of the catheter 10 of FIG. 1.

Figure 6:
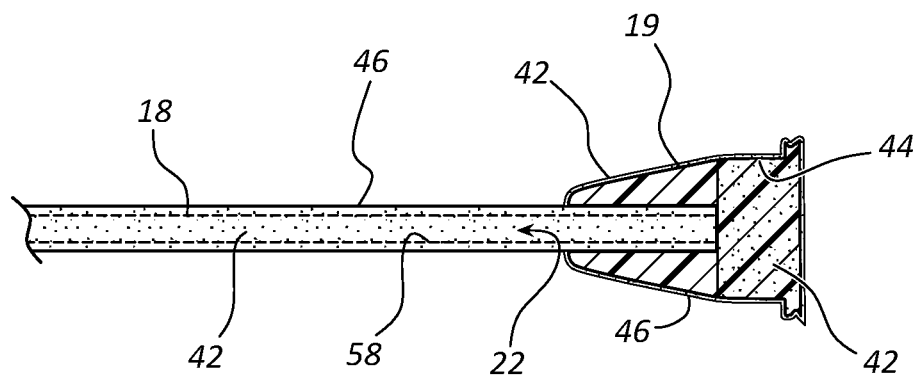
FIG. 6 illustrates a cross-section of a Luer connector connected to an extension leg of a catheter assembly in accordance with some embodiments.
Figure 7:
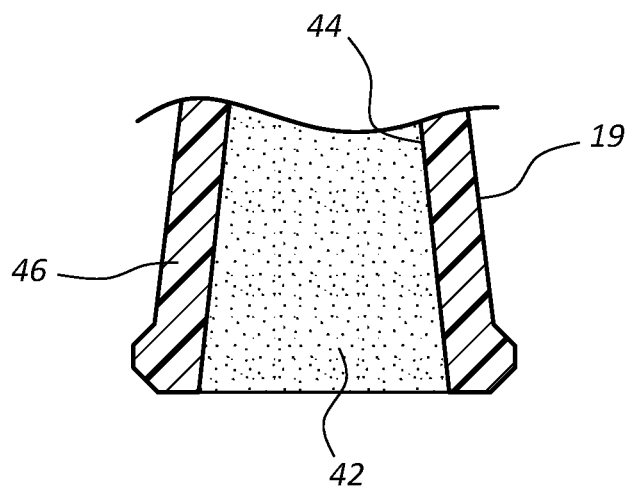
FIG. 7 illustrates a cross-section of a Luer connector of a catheter assembly in accordance with some embodiments.

In addition to the Luer connector 19, FIG. 6 also shows the internal or luminal surface 58 of the extension leg 18 of the catheter 10 of FIG. 9, or the internal or luminal surfaces 58 of the pair of extension legs 18 of the catheter 10 of FIG. 1, can include the antimicrobial coating 42. The antimicrobial coating 42 can prevent the migration of microbes from the internal surface 44 of the Luer connector 19 distally through the extension leg 18 of the catheter 10 to which the Luer connector 19 is connected. While not shown in FIG. 6, the external or abluminal surface 46 of the extension leg 18 of the catheter 10 of FIG. 9, or the external of abluminal surfaces of the pair of extension legs 18 of the catheter 10 of FIG. 1, can alternatively or additionally include the antimicrobial coating 42 between at least proximal and distal end portions thereof. Like connectors such as the Luer connector 19, the external or abluminal surfaces of extension legs like the extension leg 18 can be especially susceptible to microbial contamination due to relatively extensive physical contact by clinicians or other users of the catheter 10.

FIGS. 9 and 10 show a Luer connector 19 with a flexible valve 60 including the antimicrobial coating 42 on one or more surfaces of the Luer connector 19. The internal surface 44, the external surface 46, or both the internal and external surfaces of the Luer connector 19 include the antimicrobial coating 42. As best shown in FIG. 10, the antimicrobial coating 42 is disposed on only a proximal half of the external surface 44 of a body of the Luer connector 19, though the entirety of the external surface 46, as well as the internal surface 44, can be independently coated. Additionally or alternatively, the antimicrobial coating 42 is be disposed on a surface of the valve 60 itself.

FIG. 11 shows a threaded cap 64 used to removably cover a threaded end of the Luer connector 19 can include the antimicrobial coating 42. Indeed, both the internal surface 44 and the external surface 46 of the cap 64 can include the antimicrobial coating 42. So configured, the cap 64 can help prevent microbial contamination of the Luer connector 19 with which the cap 19 is configured to be threadably engaged. Like connectors such as the Luer connector 19, caps such as the cap 64 can be especially susceptible to microbial contamination due to relatively extensive physical contact by clinicians or other users of the catheter 10.

FIG. 12 shows a needleless connector 110 as another example of a medical device on which the antimicrobial coating 42 can be disposed in order to impart an antimicrobial effect thereto. As shown, the needleless connector 110 includes the internal surface 44 and the external surface 46, of which the internal surface 44 includes the antimicrobial coating 42. That said, the external surface 46 of the needless connector 110 can alternatively or additionally include the antimicrobial coating 42.

As an alternative to the copper-based layer 102 of the antimicrobial coating 42, FIG. 13 shows a copper-containing substance 70 incorporated into a material of a needle-penetrable septum 86 of an access port 80. The copper-containing substance 70 can be incorporated into a forming material for a medical device or a component thereof such as the septum 86 by compounding the forming material with the copper-containing substance 70 and subsequently molding (e.g., injection molding) or extruding the resulting material to provide a copper-containing medical device or a component thereof. One or more additional layers of the antimicrobial layer 42 set forth above applied to the foregoing medical device or the component thereof provides the substantially non-eluting antimicrobial coating 42 configured to provide a contact-killing antimicrobial effect. For example, the septum 86 of the port 80 can be injection molded with silicone or another medically suitable polymer compounded with the copper-containing substance 70 to provide the septum 86 with the copper-containing substance 70 incorporated therein. One or more additional layers of the antimicrobial layer 42 can be applied to the septum 86 to provide the septum 86 with the antimicrobial layer 42, the septum 86 configured to protect a reservoir 84 defined by a body of the port, as well as a fluid pathway through the port 80 together with a port stem, from microbial contamination. The septum 86 is but one example of a variety of medical devices and components that can be manufactured in this manner. In some embodiments, an entirety of the outer surface of the port body 82 includes the antimicrobial coating 42.

The embodiments described herein are merely examples of medical devices and components that can benefit from the antimicrobial coating 42. It is appreciated that a variety of medical devices can include the antimicrobial coating 42 described herein, including peripherally inserted central catheter ("PICCs"), central venous catheters ("CVCs"), hemodialysis catheters, pulmonary artery catheters, arterial catheters, urinary catheters, peritoneal dialysis catheters, enteral feeding tubes, gastrostomy tubes, nasogastric tubes, endotracheal tubes, tracheostomy tubes, umbilical catheters, needleless connectors, midlines catheters, bowel catheters, intermediate dwell catheters, Swan-Ganz catheters, implantable access ports, or other implantable devices.

It is appreciated that the antimicrobial coating 42 set forth above is useful in situations where a surface to be treated includes a relatively high durometer plastic, which is often resistant to imbibing typical antimicrobial agents for defeating viruses, bacteria, fungi, etc. Areas of a catheter that have traditionally been hard to treat include hubs such as the hub 16, any hub lumens of the hub 16, and Luer connectors such as the Luer connector 19, which often include a high durometer plastics. The antimicrobial coating 42 is employed to reduce antimicrobial colonization on fluid-carrying surfaces of medical devices such as luminal surfaces of fluid pathways through catheters or portions thereof (e.g., hubs, Luer connectors), but the antimicrobial coating 42 can also be employed on non-fluid-carrying surfaces of such medical devices.

The antimicrobial coating 42 serves as an antimicrobial surface, which reduces the likelihood of the establishment or proliferation of microbes on the antimicrobial surface. The antimicrobial coating 42 can produce at least a 4-log reduction of microbes present on the antimicrobial surface, even after an extended period of time, such as 31 days or more. The antimicrobial coating 42 is substantially non-eluting and serves as a passive barrier to colonization by microbes, including Methicillin-resistant *Staphylococcus aureus* ("MRSA"), *Pseudomonas aeruginosa, Enterobacter aerogenes*, Vancomycin-resistant *Enterococcus* ("VRE"), and yeast such as *Candida albicans*. Note that a relatively positive electrical charge of the antimicrobial coating 42 on an internal or external surface of a medical device or a component thereof enables serves as a contact-killing surface whereon microbes are immediately killed after contacting the antimicrobial surface.

FIG. 18 depicts a graph 120 showing one example of the efficacy of a copper layer such as the copper-based layer 102 when disposed on a Luer connector such as the Luer connector 19 shown in FIG. 1. FIG. 19 depicts a graph 130 showing one example of the efficacy of a copper layer such as the copper-based layer 102 when disposed on a Luer connector such as the Luer connector 19 shown in FIG. 1 and operably connected to an un-coated needleless connector such as the needleless connector 110 shown in FIG. 12. FIG. 20 depicts a graph 140 showing that suitable antimicrobial efficacy is achieved when the optional overcoat 108 is applied to a Luer connector including a copper layer such as the copper-based layer 102. Additional disclosure regarding the foregoing layers is available in U.S. Patent Publication No. 2016/0287758, published Oct. 6, 2016, which is incorporated by reference in its entirety into this application.

Methods

A method of manufacturing an antimicrobial catheter assembly such as the catheter 10 of FIG. 1 or FIG. 9 includes applying the non-eluting antimicrobial coating 42 to the internal surface 44, the external surface 46, or both the internal and external surfaces 44, 46 of one or more components of the catheter 10; and connecting the components of the catheter 10 to form the catheter 10. The antimicrobial coating 42 is a composite of two or more layers including the copper-based layer 102 between the corrosion-preventing layer 106 and the internal or external surfaces 44, 46 to which the antimicrobial coating 42 is applied, the adhesion-promoting layer 104 between the copper-based layer 102 and the internal or external surface 44, 46 to which the antimicrobial coating 42 is applied, or a combination thereof.

Applying the antimicrobial coating 42 includes applying the adhesion-promoting layer 104 to the internal or external surface 44, 46 of any component of the one or more components of the catheter 10. The adhesion-promoting layer 104 is applied to the foregoing internal or external surface 44, 46 by physical vapor deposition, chemical vapor deposition, electrodeposition, or electroless deposition of a metal selected from gold, palladium, and titanium. The internal or external surface 44, 46 to which the adhesion-promoting layer 104 is applied includes a polymer selected from polyurethane, polycarbonate, polyethylene, polypropylene, polyvinyl chloride, and silicone.

Applying the antimicrobial coating 42 includes applying the copper-based layer 102 to the internal or external surface 44, 46 of any component of the one or more components of the catheter 10. The copper-based layer 102 is applied to the foregoing internal or external surface 44, 46 by physical vapor deposition, chemical vapor deposition, electrodeposition, or electroless deposition of copper, a copper alloy, or a copper matrix composite. The internal or external surface 44, 46 to which the copper-based layer 102 is applied includes a polymer selected from polyurethane, polycarbonate, polyethylene, polypropylene, polyvinyl chloride, and silicone or the adhesion-promoting layer 104.

With respect to at least the hub 16, the copper-based layer 102 of the antimicrobial coating 42 can be deposited on the internal surface 44 of the one or more hub lumens 40 of the hub 16 by an electroless deposition process, which can deposit copper on an electrically non-conductive surface without the use of an electric field. Electroless deposition includes cleaning a surface upon which deposition is to occur before physically masking portions of any other surfaces upon which deposition should not occur. Next, the cleaned, unmasked surface is prepared by chemically or mechanically etching the surface, for example, by silicon-carbide high-pressure sand blasting.

A pre-coat layer of copper, nickel, or another suitable metal or material can then be deposited on the etched surface by electroless deposition, which can help improve the efficiency of a subsequent coating such as the copper-based layer 102. However, the pre-coat layer can be omitted. The hub 16 is then placed in a copper chloride bath where an auto-catalytic reaction forms the relatively thin, uniform copper-based layer 102 on the unmasked portions of the hub 16 as a result of an oxidation-reduction reaction.

Figure 5:
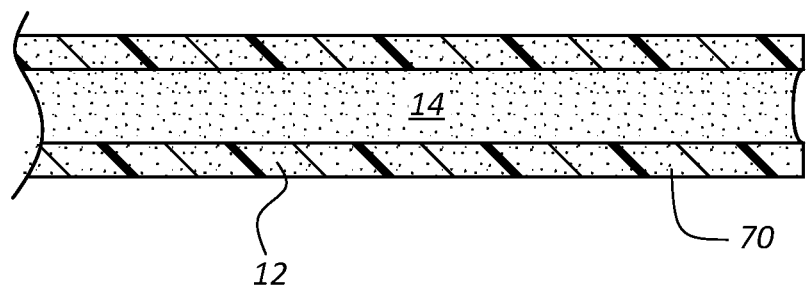
FIG. 5 illustrates a longitudinal cross-section of a catheter tube of a catheter assembly in accordance with some embodiments.

It is appreciated that other modes can be employed to provide copper-based layer 102 to the hub 16 or another component of the catheter 10. FIG. 5 gives one example of this, wherein the catheter tube 12 includes a forming material such as a resin of a thermoplastic or some other suitable polymer, which is mixed, or compounded, with the copper-containing substance 70 before being extruded into the tubular form shown in FIG. 5. Copper-containing substances that can be compounded with the resin include cuprous chloride, cupric chloride, cupric oxide, copper hydroxide, copper oxalate, copper citrate, copper gluconate, copper acetate, copper carbonate, copper sulfate, copper phosphate, other suitable copper salts, finely divided metallic copper, etc. The amount of copper-containing substance 70 by mass can vary between about 1% to about 40% by weight, though other percentages can be utilized according to need and desired outcome. The copper-containing substance can be mixed as a powder with the resin before being introduced into the extruder, where mixing and melting occurs before extrusion. The resultant catheter tube 12 or other extrudate includes a quantity of copper therein sufficient to provide a desired antimicrobial effect to internal or external surfaces.

Applying the antimicrobial coating 42 includes applying the corrosion-preventing layer 106 to the internal or external surface 44, 46 of any component of the one or more components of the catheter 10. The corrosion-preventing layer 106 is applied to the foregoing internal or external surface 44, 46 by physical vapor deposition, chemical vapor deposition, electrodeposition, or electroless deposition of gold, palladium, or titanium. The internal or external surface 44, 46 to which the corrosion-preventing layer 106 is applied includes the copper-based layer 102 or the like.

Connecting the components of the catheter 10 includes inserting the catheter tube 12 into the hub 16, inserting at least one extension leg 18 into the hub 16, and inserting the extension leg 18 into at least one Luer connector 19 to form the catheter 10. The catheter 10 has a fluid pathway defined by the internal surfaces 44 of a catheter-tube lumen 14, the hub lumen 40, and the extension-leg lumen 22.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An antimicrobial catheter assembly, comprising:
a hub including at least one hub lumen defining a corresponding hub portion of a fluid pathway through the catheter assembly;
a catheter tube connected to the hub, the catheter tube including at least one catheter-tube lumen defining a corresponding catheter-tube portion of the fluid pathway through the catheter assembly;
at least one extension leg connected to the hub, the at least one extension leg including an extension-leg lumen defining a corresponding extension-leg portion of the fluid pathway through the catheter assembly; and
a non-eluting antimicrobial coating on an internal surface of the catheter assembly, an external surface of the catheter assembly, or both the internal and external surfaces of the catheter assembly, the antimicrobial coating being a composite of three or more layers including a copper-based layer between an outer corrosion-preventing layer of a corrosion-resistant metal and an inner adhesion-promoting layer over the internal or external surface of the catheter assembly.

2. The antimicrobial catheter assembly of claim 1, wherein the inner adhesion-promoting layer includes an adhesion-promoting metal.

3. The antimicrobial catheter assembly of claim 2, wherein the adhesion-promoting metal promotes adhesion of the copper-based layer to a polymer selected from polyurethane, polycarbonate, polyethylene, polypropylene, polyvinyl chloride, and silicone.

4. The antimicrobial catheter assembly of claim 2, wherein the adhesion-promoting metal is selected from gold, palladium, and titanium.

5. The antimicrobial catheter assembly of claim 1, wherein the copper-based layer is substantially pure copper, a copper alloy of copper and gold, palladium, zinc, or tin, or a copper matrix composite of copper and tungsten.

6. The antimicrobial catheter assembly of claim 1, wherein the corrosion-resistant metal is selected from gold, palladium, and titanium.

7. The antimicrobial catheter assembly of claim 1, wherein the non-eluting antimicrobial coating is on the internal surface of the catheter assembly including the at least one hub lumen defining the corresponding hub portion of the fluid pathway through the catheter assembly.

8. The antimicrobial catheter assembly of claim 1, wherein the non-eluting antimicrobial coating is on the internal surface of the catheter assembly including the extension-leg lumen defining the corresponding extension-leg portion of the fluid pathway through the catheter assembly.

9. The antimicrobial catheter assembly of claim 1, wherein the non-eluting antimicrobial coating is on the external surface of the catheter assembly including an abluminal surface of the at least one extension leg between at least proximal and distal end portions of the at least one extension leg.

10. The antimicrobial catheter assembly of claim 1, wherein the non-eluting antimicrobial coating is on the external surface of the catheter assembly including an abluminal surface of a transcutaneous region of the catheter tube.

11. The antimicrobial catheter assembly of claim 1, further comprising at least one Luer connectorconnected to the at least one extension leg, the non-eluting antimicrobial coating on the internal surface of the catheter assembly including an internal surface of the at least one Luer connector in fluid communication with the fluid pathway, an external surface of the catheter assembly including an external surface of the at least one Luer connector, or combination thereof.

12. An antimicrobial catheter assembly, comprising:
a bifurcated hub including a pair of hub lumens defining corresponding hub portions of a pair of fluid pathways through the catheter assembly;
a catheter tube connected to the bifurcated hub, the catheter tube including a pair of catheter-tube lumens defining corresponding catheter-tube portions of the pair of fluid pathways through the catheter assembly;
a pair of extension legs connected to the bifurcated hub, each extension leg including an extension-leg lumen defining a corresponding extension-leg portion of the pair of fluid pathways through the catheter assembly;
a pair of Luer connectors, each Luer connector connected to an extension leg of the pair of extension legs; and
a non-eluting antimicrobial coating on an internal surface of the catheter assembly, an external surface of the catheter assembly, or both the internal and external surfaces of the catheter assembly, the non-eluting antimicrobial coating being a composite of three or more layers including a copper-based layer between an outer corrosion-preventing layer of a corrosion-resistant metal and an inner adhesion-promoting layer over the internal or external surface of the catheter assembly.

13. The antimicrobial catheter assembly of claim 12, wherein the inner adhesion-promoting layer promotes adhesion of the copper-based layer to a polymer selected from polyurethane, polycarbonate, polyethylene, polypropylene, polyvinyl chloride, and silicone, the inner adhesion-promoting layer including a metal selected from gold, palladium, and titanium.

14. The antimicrobial catheter assembly of claim 12, wherein the copper-based layer is substantially pure copper, a copper alloy of copper and gold, palladium, zinc, or tin, or a copper matrix composite of copper and tungsten.

15. The antimicrobial catheter assembly of claim 12, wherein the corrosion-resistant metal is selected from gold, palladium, and titanium.

16. The antimicrobial catheter assembly of claim 12, wherein the non-eluting antimicrobial coating is on the internal surface of the catheter assembly including the pair of hub lumens defining the corresponding hub portions of the pair of fluid pathways through the catheter assembly.

17. The antimicrobial catheter assembly of claim 12, wherein the non-eluting antimicrobial coating is on the internal surface of the catheter assembly including the extension-leg lumens defining the corresponding extension-leg portions of the pair of fluid pathways through the catheter assembly.

18. The antimicrobial catheter assembly of claim 12, wherein the non-eluting antimicrobial coating is on the internal surface of the catheter assembly including an internal surface of each Luer connector defining a corresponding Luer-connector portion of the pair of fluid pathways through the catheter assembly, the external surface of catheter assembly including an external surface of each Luer connector, or a combination thereof.

19. The antimicrobial catheter assembly of claim 12, wherein the non-eluting antimicrobial coating is on the external surface of the catheter assembly including abluminal surfaces of the pair of extension legs between at least proximal and distal end portions of each extension leg.

20. The antimicrobial catheter assembly of claim 12, wherein the non-eluting antimicrobial coating is on the external surface of the catheter assembly including an abluminal surface of a transcutaneous region of the catheter tube.

* * * * *